United States Patent
Freeman et al.

(10) Patent No.: US 11,291,830 B2
(45) Date of Patent: *Apr. 5, 2022

(54) UNIVERSAL DEFIBRILLATION ELECTRODE PAD ASSEMBLY FOR ADULT AND PEDIATRIC SUBJECTS

(71) Applicant: ZOLL Medical Corporation, Chelmsford, MA (US)

(72) Inventors: Gary A. Freeman, Waltham, MA (US); Ward Hamilton, Amherst, NH (US); Deborah T. Jones, Dartmouth, MA (US); David N. Craige, III, Attleboro, MA (US); Melissa M. Dascoli, Wakefield, MA (US); E. Jane Wilson, Hingham, MA (US); Ian B. Durrant, Arlington, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 184 days.

This patent is subject to a terminal disclaimer.

(21) Appl. No.: 16/231,443

(22) Filed: Dec. 22, 2018

(65) Prior Publication Data
US 2019/0117954 A1 Apr. 25, 2019

Related U.S. Application Data

(63) Continuation of application No. 14/494,084, filed on Sep. 23, 2014, now Pat. No. 10,201,696.
(Continued)

(51) Int. Cl.
*A61N 1/04* (2006.01)
*A61H 31/00* (2006.01)
(Continued)

(52) U.S. Cl.
CPC ............. *A61N 1/046* (2013.01); *A61H 31/00* (2013.01); *A61H 31/004* (2013.01);
(Continued)

(58) Field of Classification Search
CPC ........ A61N 1/046; A61N 1/0492; A61N 1/08; A61N 1/0472; A61H 31/004; A61H 31/00; A61B 5/0408; A61B 5/6823
See application file for complete search history.

(56) References Cited

U.S. PATENT DOCUMENTS 5,243,978 A 9/1993 Duffin, Jr.
6,141,584 A 10/2000 Rockwell et al.
(Continued)

FOREIGN PATENT DOCUMENTS

CN 1555278 A 12/2004
CN 101084040 A 12/2007
(Continued)

OTHER PUBLICATIONS

Aramendi et al. "A Simple Effective Filtering Method for Removing CPR Caused Artefacts from Surface ECG Signals", Computers in Cardiology, Sep. 25, 2005.
(Continued)

*Primary Examiner* — Jennifer Pitrak McDonald
*Assistant Examiner* — Pamela M. Bays
(74) *Attorney, Agent, or Firm* — The Webb Law Firm

(57) ABSTRACT

A defibrillation electrode pad includes an electrode section and a CPR administration section. The electrode section and the CPR administration section are positioned in the defibrillation electrode pad relative to each other such that the CPR administration section is located above a sternum of an adult subject and the electrode section is located in a position appropriate for the administration of a defibrillation shock to the adult subject when the defibrillation electrode pad is
(Continued)

oriented in a first orientation and such that the CPR administration section is located above a sternum of a pediatric subject and the electrode section is located in a position appropriate for the administration of a defibrillation shock to the pediatric subject when the defibrillation electrode pad is oriented in a second orientation different from the first orientation.

31 Claims, 7 Drawing Sheets

Related U.S. Application Data

(60) Provisional application No. 61/884,264, filed on Sep. 30, 2013.

(51) Int. Cl.
  *A61N 1/08* (2006.01)
  *A61N 1/39* (2006.01)
  *A61B 5/00* (2006.01)
  *A61B 5/25* (2021.01)

(52) U.S. Cl.
  CPC .............. *A61N 1/0492* (2013.01); *A61B 5/25* (2021.01); *A61B 5/6823* (2013.01); *A61B 5/6841* (2013.01); *A61H 31/005* (2013.01); *A61H 31/007* (2013.01); *A61H 2031/002* (2013.01); *A61N 1/0472* (2013.01); *A61N 1/08* (2013.01); *A61N 1/3993* (2013.01)

(56) References Cited

U.S. PATENT DOCUMENTS

| | | | |
|---|---|---|---|
| 6,148,233 A | 11/2000 | Owen et al. | |
| 6,356,785 B1 | 3/2002 | Snyder et al. | |
| 6,405,083 B1 | 6/2002 | Rockwell et al. | |
| 6,427,685 B1 | 8/2002 | Ray, III | |
| 6,438,417 B1 | 8/2002 | Rockwell et al. | |
| 6,597,948 B1 | 7/2003 | Rockwell et al. | |
| 6,782,293 B2 | 8/2004 | Dupelle et al. | |
| 6,920,354 B2 | 7/2005 | Daynes et al. | |
| 7,231,258 B2 | 6/2007 | Moore et al. | |
| 7,769,465 B2 | 8/2010 | Matos | |
| 9,079,044 B2 | 7/2015 | Powers | |
| 2001/0047140 A1 | 11/2001 | Freeman | |
| 2003/0045905 A1 | 3/2003 | Daynes et al. | |
| 2003/0055459 A1 | 3/2003 | Lyster et al. | |
| 2003/0055477 A1 | 3/2003 | Dupelle et al. | |
| 2003/0088276 A1 | 5/2003 | Covey et al. | |
| 2003/0171798 A1 | 9/2003 | Nova et al. | |
| 2004/0143298 A1 | 7/2004 | Nova et al. | |
| 2004/0210170 A1 | 10/2004 | Palazzolo et al. | |
| 2005/0010274 A1 | 1/2005 | Dupelle et al. | |
| 2005/0131465 A1 | 6/2005 | Freeman et al. | |
| 2005/0267536 A1* | 12/2005 | Freeman | A61N 1/39044 607/5 |
| 2006/0015044 A1 | 1/2006 | Stavland et al. | |
| 2006/0019229 A1* | 1/2006 | Morallee | A61H 31/00 434/265 |
| 2007/0196320 A1 | 8/2007 | Yasin | |
| 2007/0197926 A1 | 8/2007 | Danehorn et al. | |
| 2007/0233199 A1 | 10/2007 | Moore et al. | |
| 2007/0299473 A1 | 12/2007 | Matos | |
| 2008/0004663 A1 | 1/2008 | Jorgenson | |
| 2008/0027338 A1 | 1/2008 | Lu et al. | |
| 2009/0254136 A1* | 10/2009 | Powers | A61N 1/3993 607/5 |
| 2010/0004710 A1 | 1/2010 | Kellum | |
| 2010/0164612 A1 | 7/2010 | Koyrakh | |
| 2010/0292748 A9 | 11/2010 | Stickney et al. | |
| 2010/0324612 A1 | 12/2010 | Matos | |
| 2011/0034836 A1 | 2/2011 | Halperin et al. | |
| 2011/0105930 A1 | 5/2011 | Thiagarajan et al. | |
| 2011/0112593 A1* | 5/2011 | Freeman | A61B 5/02438 607/6 |
| 2011/0288604 A1 | 11/2011 | Kaib et al. | |
| 2012/0146797 A1 | 6/2012 | Oskin et al. | |
| 2012/0185006 A1 | 7/2012 | Apperson et al. | |
| 2013/0102936 A1 | 4/2013 | Halsne et al. | |
| 2016/0082246 A1* | 3/2016 | Piazza | A61N 1/0408 607/5 |

FOREIGN PATENT DOCUMENTS

| | | |
|---|---|---|
| CN | 101557788 A | 10/2009 |
| DE | 3110915 A1 | 12/1982 |
| JP | 2008523878 A | 7/2008 |
| JP | 201029728 A | 2/2010 |
| WO | 2013032710 A1 | 3/2013 |

OTHER PUBLICATIONS

Associate for the Advancement of Medical Instrumentation, ANSI/AAMI DF:80:2003, Medical Electrical Equipment—Part 2-4: Particular Requirements for the Safety of Cardiac Defibrillators (including Automated External Defibrillators) 2004, ISBN 1-57020-210-9, abstract, p. vi, p. 50, section 107.1.2.

Romero et al. "Motion Artifact Reduction in Ambulatory ECTG Monitoring: An Integrated System Approach", Wireless Health, Oct. 10, 2011.

International Search Report from corresponding PCT Application Serial No. PCT/US2014/056980, dated Jan. 9, 2015.

Written Opinion from corresponding PCT Application Serial No. PCT/US2014/056980, dated Jan. 9, 2015.

* cited by examiner

UNIVERSAL DEFIBRILLATION ELECTRODE PAD ASSEMBLY FOR ADULT AND PEDIATRIC SUBJECTS

RELATED APPLICATIONS

This application is a continuation of U.S. patent application Ser. No. 14/494,084, titled "UNIVERSAL DEFIBRILLATION ELECTRODE PAD ASSEMBLY FOR ADULT AND PEDIATRIC SUBJECTS", filed on Sep. 23, 2014, now U.S. Pat. No. 10,201,696 which claims priority under 35 U.S.C. § 119(e) to U.S. Provisional Application Ser. No. 61/884,264, titled "UNIVERSAL DEFIBRILLATION ELECTRODE PAD ASSEMBLY FOR ADULT AND PEDIATRIC SUBJECTS," filed on Sep. 30, 2013, which is herein incorporated by reference in its entirety.

BACKGROUND

Technical Field

Aspects and embodiments of the present invention relate to systems and methods for the treatment of individuals experiencing cardiac distress.

Discussion of Related Art

Treatment of a subject experiencing cardiac distress may generally include clearing the subject's airway, assisting the subject's breathing, chest compressions, and defibrillation.

Defibrillation can be performed with the use of an automatic external defibrillator (AED). Most automatic external defibrillators are actually semi-automatic external defibrillators (SAED), which require a clinician to press a start button, after which the defibrillator analyzes the subject's condition and provides a shock to the subject if the electrical rhythm is shockable and waits for user intervention before any subsequent shock. Fully automatic external defibrillators, on the other hand, do not wait for user intervention before applying subsequent shocks. As the term is used herein, automatic external defibrillators (AED) include semi-automatic external defibrillators (SAED).

Defibrillation shocks are typically delivered to a subject from a defibrillator through a set of defibrillation electrodes placed on the body of the subject. The electrodes are placed in electrical communication with the skin of the subject in locations that will direct an electrical charge supplied through the electrodes through the heart of the subject.

In some instances, one or more defibrillation electrodes may be provided in a defibrillation electrode pad assembly including a CPR administration area. The CPR administration area may be a portion of the defibrillation electrode pad assembly through which a first responder may apply chest compressions to a subject during the administration of CPR. The CPR administration area may be displaced from defibrillation electrodes in the defibrillation electrode pad assembly.

It is often desirable to arrange the defibrillation electrodes and CPR administration area in a defibrillation electrode pad assembly such that the relative positioning of the defibrillation electrodes and the CPR administration area provide for each to be located on an appropriate location of a subject when the defibrillation electrode pad assembly is applied to the subject. For subjects of different sizes, for example, pediatric subjects versus adult subjects, it has in the past been necessary to provide differently sized defibrillation electrode pad assemblies such that the distance between the defibrillation electrodes and the CPR administration area allows for each to be located properly on the differently sized subjects.

SUMMARY

In accordance with a first aspect, there is provided a defibrillation electrode pad. The defibrillation electrode pad comprises an electrode section and a CPR administration section mechanically coupled to the electrode section. The electrode section and the CPR administration section are positioned in the defibrillation electrode pad relative to each other such that the CPR administration section is located above a sternum of an adult subject and the electrode section is located in a position appropriate for the administration of a defibrillation shock to the adult subject when the defibrillation electrode pad is oriented in a first orientation and such that the CPR administration section is located above a sternum of a pediatric subject and the electrode section is located in a position appropriate for the administration of a defibrillation shock to the pediatric subject when the defibrillation electrode pad is oriented in a second orientation different from the first orientation. In some embodiments, the first orientation is rotated by approximately 180 degrees from the second orientation.

In some embodiments, the position appropriate for the administration of a defibrillation shock to the adult subject is an apex position on the chest of the adult subject. The position appropriate for the administration of a defibrillation shock to the pediatric subject may be a lateral position on the pediatric subject.

In some embodiments, the defibrillation electrode pad further comprises indicia of a proper orientation of the defibrillation electrode pad for an adult subject and a proper orientation of the defibrillation electrode pad for a pediatric subject. The defibrillation electrode pad may further comprise a CPR assistance device configured to provide feedback regarding the frequency and/or depth of chest compressions applied to the subject during the administration of CPR to the subject.

In accordance with another aspect, there is provided a method of treating a subject experiencing cardiac distress. The method comprises obtaining a universal defibrillation electrode pad and a defibrillator, determining a proper orientation of the universal defibrillation electrode pad on the subject, applying the universal defibrillation electrode pad to the subject in the proper orientation, and administering therapy to the subject using the universal defibrillation electrode pad.

In some embodiments, the method further comprises applying a second electrode pad to the subject. The method may also further comprise electrically coupling the universal defibrillation electrode pad and the second electrode pad to a defibrillator.

In some embodiments, determining the proper orientation of the universal defibrillation electrode pad comprises determining an orientation of the universal defibrillation electrode pad from indicia of proper orientation provided on the universal defibrillation electrode pad.

In some embodiments, administering therapy to the subject comprises applying chest compressions to the subject through a CPR administration area of the universal defibrillation electrode pad and in some embodiments, administering therapy to the subject comprises applying a defibrillation shock to the subject through an electrode of the universal defibrillation electrode pad.

In some embodiments, the method further comprises physically decoupling an electrode section of the defibrillation electrode pad from a CPR administration section of the defibrillation electrode pad. Physically decoupling the electrode section of the defibrillation electrode pad from the CPR administration section of the defibrillation electrode pad may comprise tearing a bridge of material which physically couples the electrode section to the CPR administration section. Applying the universal defibrillation electrode pad to the subject may comprise separately attaching the electrode section and the CPR administration section to the subject.

In accordance with another aspect, there is provided defibrillation electrode pad. The defibrillation electrode pad includes an electrode section, a CPR administration section, means for providing an indication of a proper orientation of the defibrillation electrode pad on an adult subject, and means for providing an indication of a proper orientation of the defibrillation electrode pad on a pediatric subject.

In some embodiments, the electrode section is mechanically coupled to the CPR administration section by a bridge of material. The bridge of material may include a semi-rigid material configured to provide for the electrode section and the CPR administration section to remain in a fixed orientation relative to one another and separated by a fixed distance from one another. The bridge of material may include a deformable material configured to provide for the relative orientation and distance between the electrode section and the CPR administration section to be varied. In other embodiments, the electrode section is physically unconnected to the CPR administration section. The bridge of material may include one or more perforations configured to provide for the electrode section to be detached from the CPR administration section by cutting or tearing along the one or more perforations.

In some embodiments, the means for providing the indication of the proper orientation of the defibrillation electrode pad indicates that the proper orientation of the defibrillation electrode pad on the adult subject is inverted from the proper orientation of the defibrillation electrode pad on the pediatric subject. The means for providing the indication of the proper orientation of the defibrillation electrode pad may include one of a visual indicator and a tactile indicator of the proper orientation of the defibrillation electrode pad on a subject.

In some embodiments, the CPR administration section includes a displacement sensor. The CPR administration section may further include a CPR assistance device configured to provide feedback regarding frequency and/or depth of chest compressions applied to a subject on which the defibrillation electrode pad is disposed during the administration of CPR to the subject.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
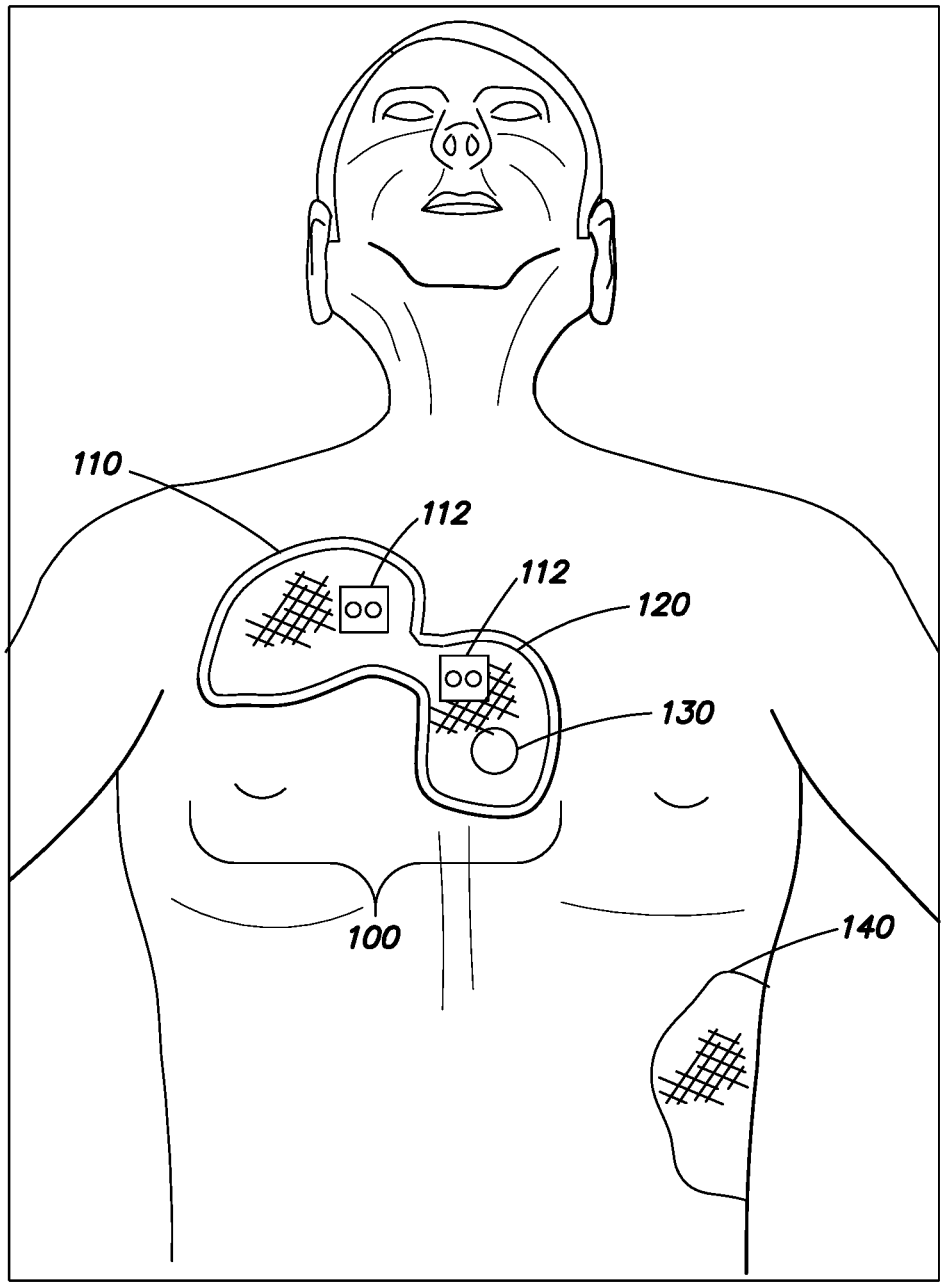
FIG. 1 is a drawing of an embodiment of a defibrillation electrode pad applied to an adult subject.

Aspects and embodiments of the present invention are not limited to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof.

Aspects and embodiments of the present invention include systems and methods which may facilitate the use of a universal treatment pad for defibrillation and/or administration of CPR to both adult and pediatric subjects. The provision of a universal treatment pad for both adult and pediatric subjects may eliminate the need to provide multiple differently sized treatment pads with a defibrillation apparatus for the treatment of adult subjects and pediatric subjects. The provision of a universal treatment pad may prevent errors associated with using an inappropriate treatment pad on a subject and locating a defibrillation electrode and/or CPR treatment area of the treatment pad in positions on the subject which are non-optimal for treatment of the subject.

FIG. 1 illustrates an embodiment of a defibrillation electrode pad assembly 100 placed on the body of an adult subject. The defibrillation electrode pad assembly 100 includes an electrode section 110 and a CPR administration section 120. The electrode section 110 includes at least one defibrillation electrode for delivering a defibrillation shock to the subject from a defibrillator electrically coupled to the at least one defibrillation electrode. The at least one defibrillation electrode may, in some embodiments, be utilized to monitor ECG signals from the subject when not being used for defibrillation. The CPR administration section 120 includes a region through which a first responder may apply chest compressions to the subject. The CPR administration section 120 may include legends to indicate proper placement of the CPR administration section 120 on the subject and the proper placement of the heel of the first responder's hand for administration of CPR. The defibrillation electrode pad assembly 100 may include at least one electrical connector 112 through which the electrode section 110 may be coupled to an external device, for example, a monitor or defibrillator and/or through which the CPR administration section 120 may be electrically coupled to an external CPR administration monitor/feedback device. It should be appreciated that is some embodiments, only a single electrical connector 112 may be provided for coupling the electrode section 110 and the CPR administration section 120 to an external device.

In some embodiments, the CPR administration section 120 may include a displacement sensor 130, for example, as described in co-pending U.S. patent application Ser. No. 14/313,772 which is incorporated herein by reference. The displacement sensor 130, which may include an accelerometer, may be utilized to monitor the frequency and/or depth of CPR compressions and provide this information to a system which may provide feedback to the first responder to alter the frequency and/or depth of chest compressions as necessary to achieve a desirable CPR administration routine. A CPR assistance device, for example, the PocketCPR® CPR assistance device available from ZOLL Medical Corporation or one of the CPR assistance devices disclosed in U.S. Patent Nos. 7,245,974, 8,096,962, 6,390,996, 6,782,293, 7,108,665, 7,118,542, and 7,122,014 may be used to facilitate the administration of CPR through the CPR administration section 120 and/or may be incorporated into the CPR administration section 120. One or both of the electrode section 110 and CPR administration section 120 may further include one or more monitoring or pacing electrodes and/or a pulse oximetry or perfusion monitor as also described in co-pending U.S. patent application Ser. No. 14/313,772. Defibrillation electrode(s) in the electrode section 110 may, in some embodiments, be utilized to monitor ECG signals from the subject when not being used for defibrillation.

In FIG. 1, the electrode section 110 is located in an apex position of the chest of the adult subject. A defibrillation electrode located in the apex position as illustrated may be utilized with a second electrode patch 140 coupled to the subject on a lateral position of the thorax of the subject as illustrated to deliver defibrillation shocks to the subject. The second electrode patch 140 includes at least one defibrillation electrode and may also include monitoring and/or pacing electrodes, ECG monitoring electrodes, and/or pulse oximetry or other subject status monitors. In some embodiments, one or more electrodes in the second electrode patch 140 may be used for multiple purposes, for example, for both defibrillation and ECG monitoring. The CPR administration section 120 is positioned over the sternum of the subject, which is a desirable location at which to administer chest compressions during the performance of CPR. The relative locations of the electrode section 110 and the CPR administration section 120 in the defibrillation electrode pad assembly 100 provide for both of these sections 110, 120 to be located at desirable positions on the subject.

The relative locations of the electrode section 110 and the CPR administration section 120 in the defibrillation electrode pad assembly 100 may not be conducive to locating the electrode section 110 in an apex position and the CPR administration section 120 on the sternum of a subject having a body size significantly different from the adult subject illustrated in FIG. 1. For example, in a pediatric subject the distance between the apex position and the subject's sternum may be less than the distance between the electrode section 110 and the CPR administration section 120 in the defibrillation electrode pad assembly 100.

However, a properly dimensioned defibrillation electrode pad assembly 100 may be utilized for both adult and pediatric subjects. Positioning the defibrillation electrode pad assembly 100 in a first orientation may provide for the electrode section 110 and the CPR administration section 120 of the defibrillation electrode pad assembly 100 to be located in desirable positions on an adult subject. Positioning the defibrillation electrode pad assembly 100 in a second orientation may provide for the electrode section 110 and the CPR administration section 120 of the defibrillation electrode pad assembly 100 to be located in desirable positions on a pediatric subject.

Figure 2A:
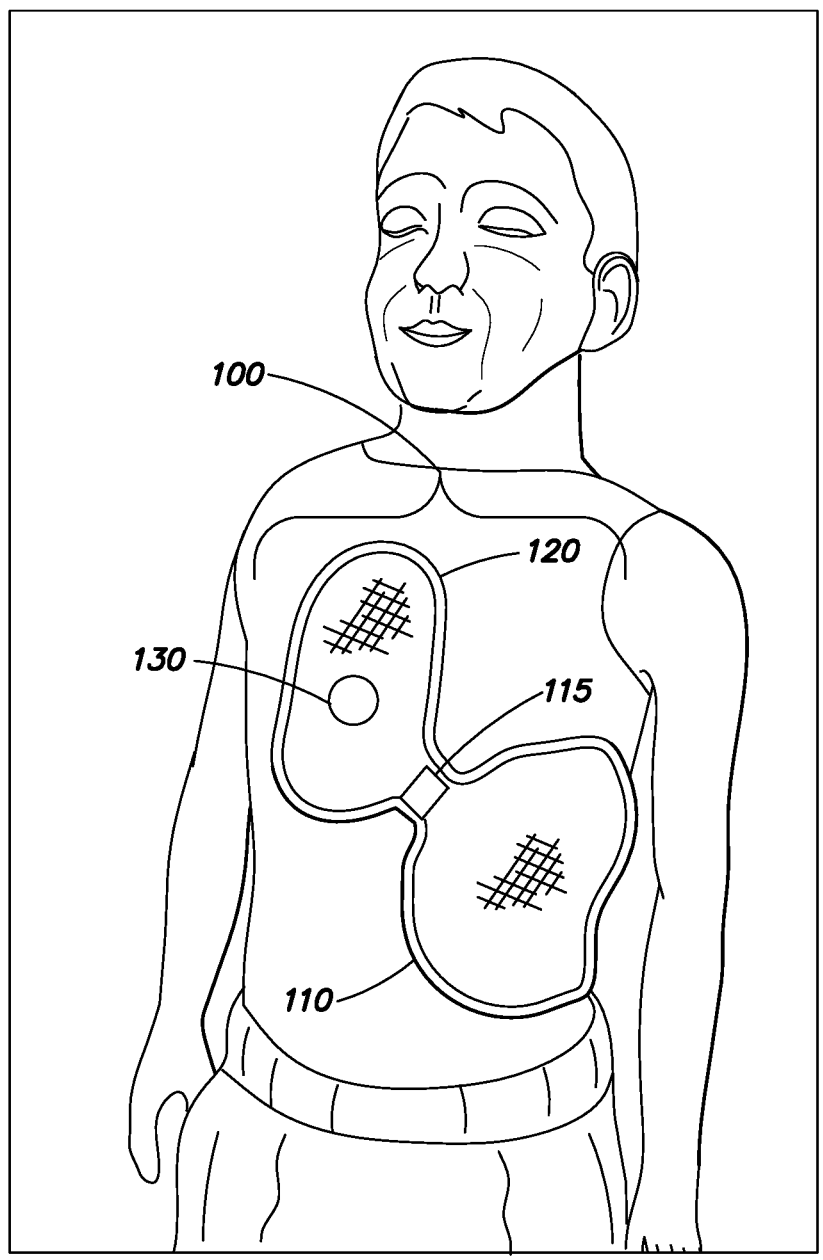
FIG. 2A is a drawing of the defibrillation electrode pad of FIG. 1 applied to a pediatric subject.
Figure 2B:
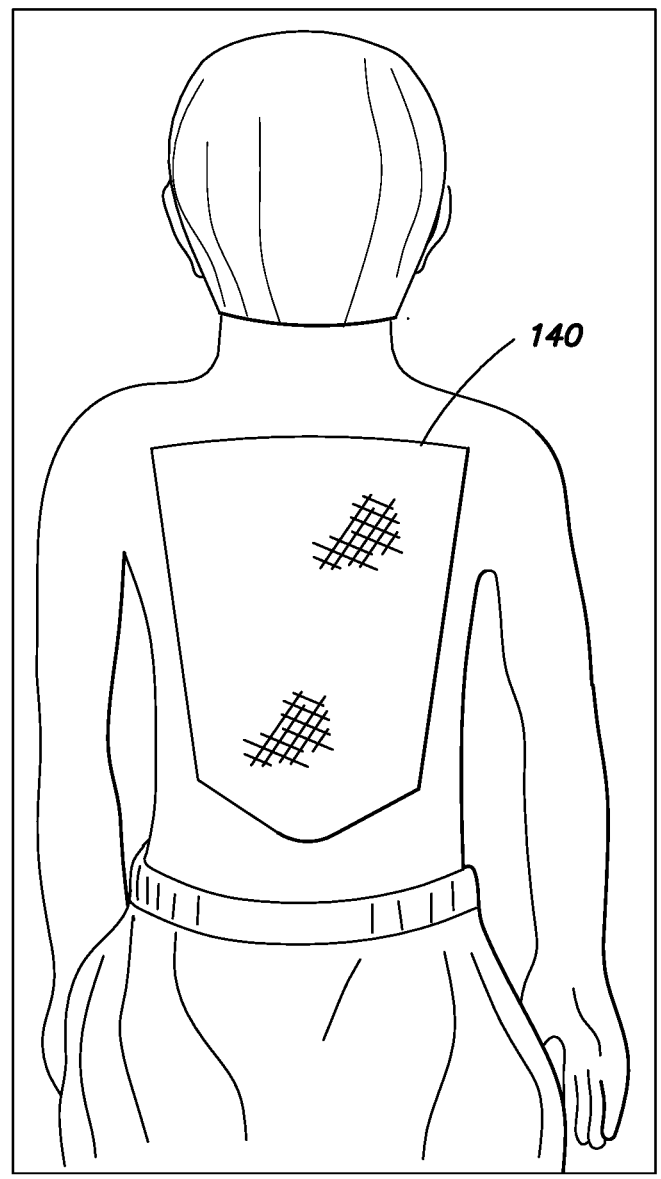
FIG. 2B is a drawing of a second electrode pad applied to a pediatric subject.

FIG. 2A illustrates the defibrillation electrode pad assembly 100 of FIG. 1 placed on a pediatric subject. The defibrillation electrode pad assembly 100 has been rotated by about 180 degrees as compared to its orientation on the adult subject in FIG. 1 to provide for proper positioning of the electrode section 110 and the CPR administration section 120 on the pediatric subject in FIG. 2A. In FIG. 2A, the CPR administration section 120 is located on the sternum of the subject, while the electrode section 110 is located on a lateral position on the thorax of the subject. Lateral positioning of the electrode section 110 provides for an acceptable delivery of a defibrillation shock to the subject when the second electrode patch 140 is located on the rear of the subject, as illustrated in FIG. 2B. In some embodiments, the defibrillation electrode pad assembly 100 may be properly oriented on a subject in orientations other than illustrated in FIGS. 1 and 2A. For example, the defibrillation electrode pad assembly 100 may be rotated by less than about 180 degrees as compared to its orientation on the adult subject in FIG. 1 to properly position the electrode section 110 and the CPR administration section 120 on a smaller adult subject.

As illustrated in FIGS. 1 and 2A, the electrode pad assembly 100 may include an electrode section 110 and a CPR administration section 120 which are separated by a set distance by a bridge of material 115. In some embodiments, the bridge of material 115 may include a non-conductive material which may be a same or similar material as one which is used to cover an outer surface of the electrode section 110 and/or CPR administration section 120. The bridge of material 115 may be rigid or semi-rigid, for example, including a rigid or semi-rigid plastic sheet and/or metal sheet or wire, to provide for the electrode section 110 and the CPR administration section 120 to remain in a fixed orientation relative to one another and/or separated by a fixed distance from one another. Alternatively, the bridge of material 115 may include a deformable material, for example, a sheet of fabric and/or polymeric material, which may provide for the relative orientation and/or distance between the electrode section 110 and the CPR administration section 120 to be varied.

Figure 2C:
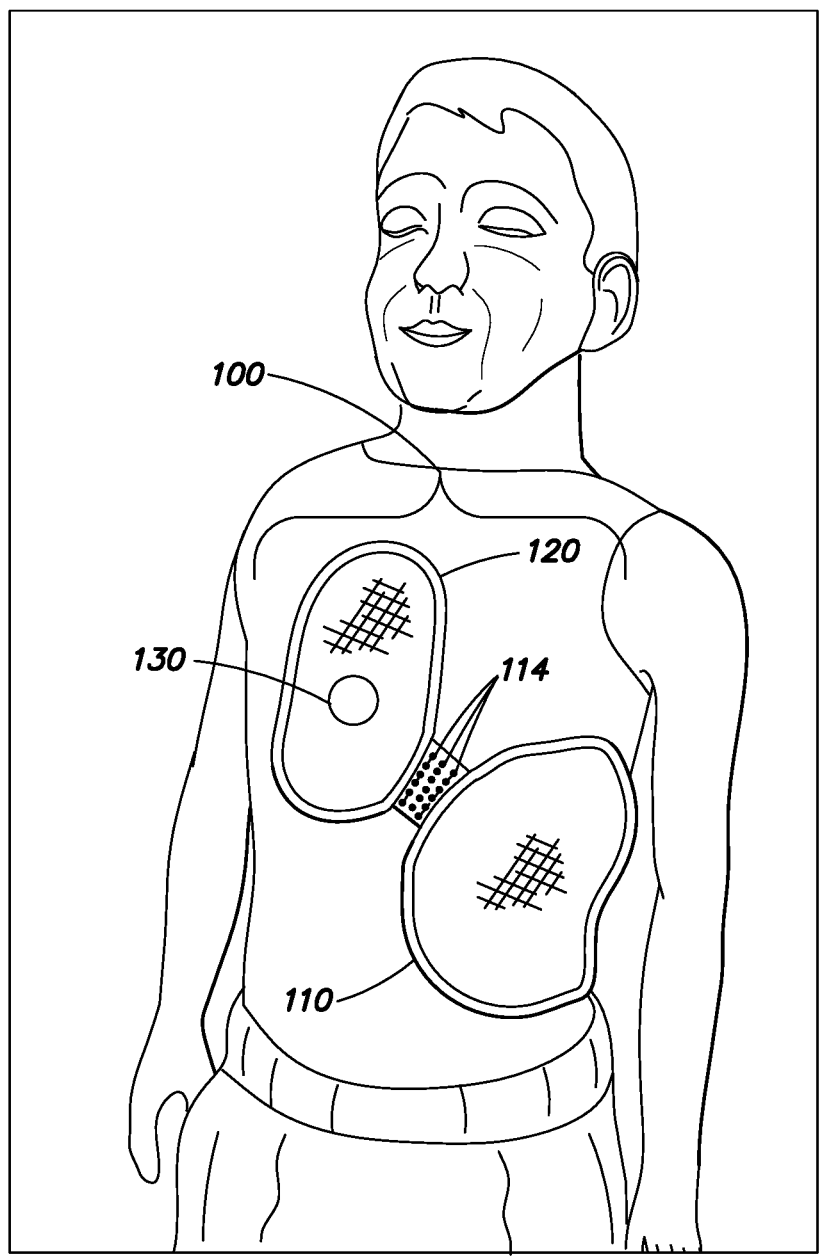
FIG. 2C is a drawing of another embodiment of a defibrillation electrode pad applied to a pediatric subject.

As illustrated in FIG. 2C, in some embodiments, the bridge of material 115 may include one or more perforations 114 along ends of the bridge of material proximate the electrode section 110 and/or the CPR administration section 120 and/or through a central portion of the bridge of material 115. The perforations 114 may also be in the form of thinned portions of the bridge of material 115 or score lines in the bridge of material 115. These perforations 114 may provide for a caregiver or first responder to detach the electrode section 110 from the CPR administration section 120. It may be desirable to detach the electrode section 110 from the CPR administration section 120 if the bridge of material 115 would otherwise maintain the electrode section 110 and the CPR administration section 120 in relative orientations and/or with a separation distance which would be inappropriate for a particular subject. A caregiver or first responder can physically decouple the electrode section 110 from the CPR administration section 120 by tearing the bridge of material 115 along one or more of the perforations 114 and place the electrode section 110 and the CPR administration section 120 at appropriate locations on the subject or utilize only one of the electrode section 110 or the CPR administration section 120 while leaving the other unattached to the subject.

Figure 2D:
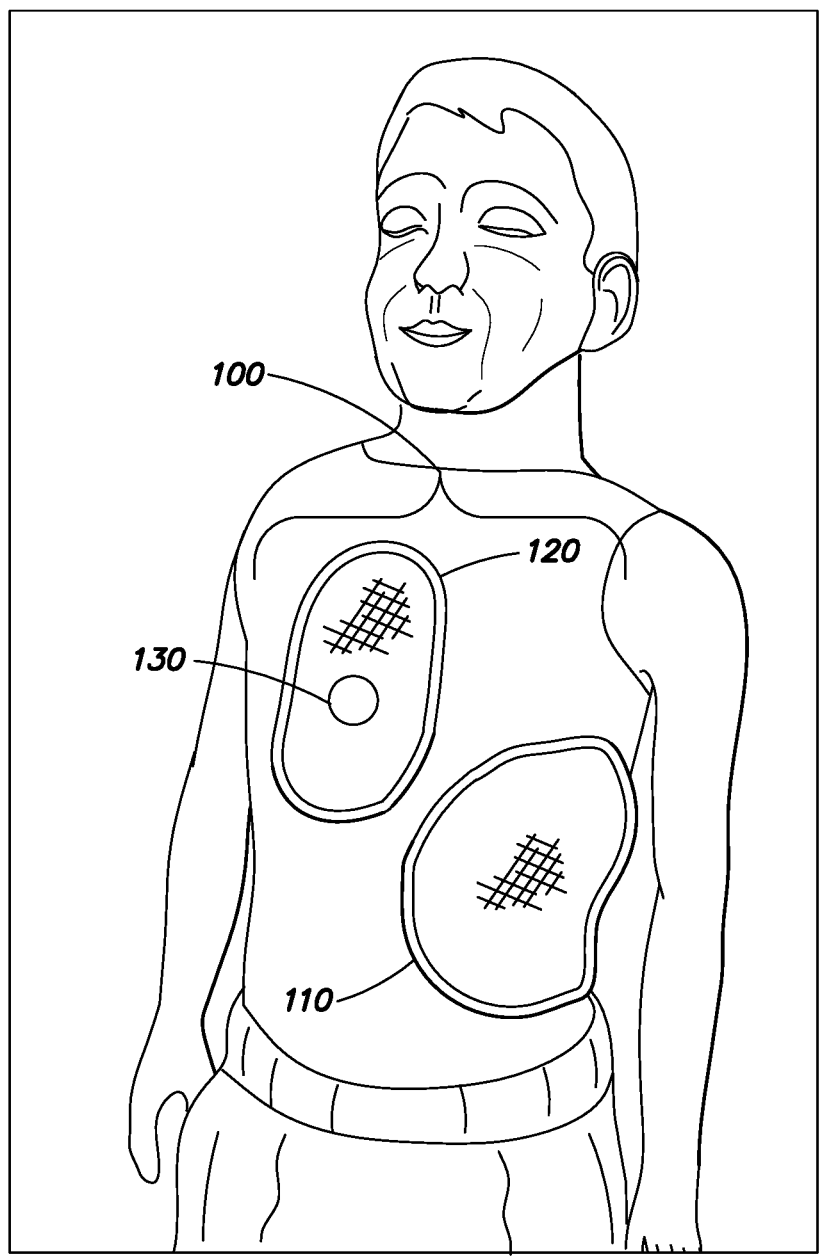
FIG. 2D is a drawing of an electrode and a CPR administration pad applied to a pediatric subject.

As illustrated in FIG. 2D, the bridge of material 115 may be omitted (or removed along the perforations 114 of FIG. 2C) and the electrode section 110 and the CPR administration section 120 may be physically separated unconnected distinct elements. The electrode section 110 and the CPR administration section 120 may be considered physically separated and unconnected even though they may be indirectly physically connected by, for example, one or more electrical conductors running between the electrode section 110 and the CPR administration section 120 or between the electrode section 110 and a therapy device, for example a monitor or defibrillator, which is also electrically coupled to the CPR administration section 120.

Figure 3:
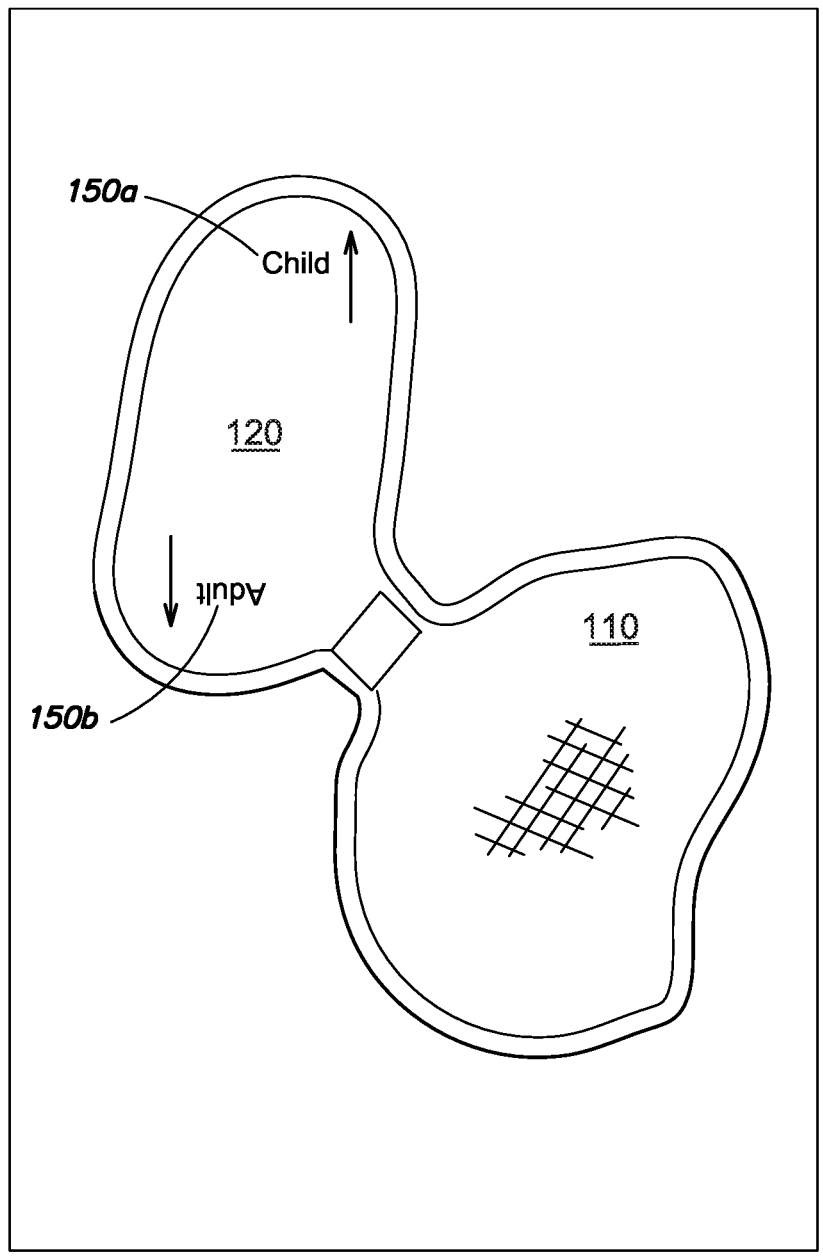
FIG. 3 is a drawing of labels included on embodiments of a defibrillation electrode pad.

In some embodiments, the defibrillation electrode pad assembly 100 may include markings or labels to help a first responder determine how to orient the defibrillation electrode pad assembly 100 on a subject. For example, as illustrated in FIG. 3, labels 150a and 150b may be provided on a portion of the defibrillation electrode pad assembly 100, for example, the CPR administration section 120 and/or the electrode section 110, with arrows indicating which portion of the CPR administration section 120 should be positioned in an upward orientation for an adult subject and for a child subject. The labels 150a, 150b may include words such as "child" and "adult," which may be provided in multiple languages, and/or may include symbols or graphical representations, for example, an image of a child and/or an image of an adult, which may help a first responder determine how to orient the defibrillation electrode pad assembly 100 on a subject. The defibrillation electrode pad assembly 100 may alternatively or additionally include labels 150a and 150b having one or more raised symbols or characters to provide a tactile indication of the proper orientation of the defibrillation electrode pad 100 on an adult and/or pediatric subject.

The defibrillation electrode pad assembly 100 and second electrode patch 140 may be used with a number of different defibrillators, for example, any one of the many defibrillators or AEDs available from ZOLL Medical Corporation. Aspects of the present invention are not limited to use with any particular defibrillator.

Figure 4:
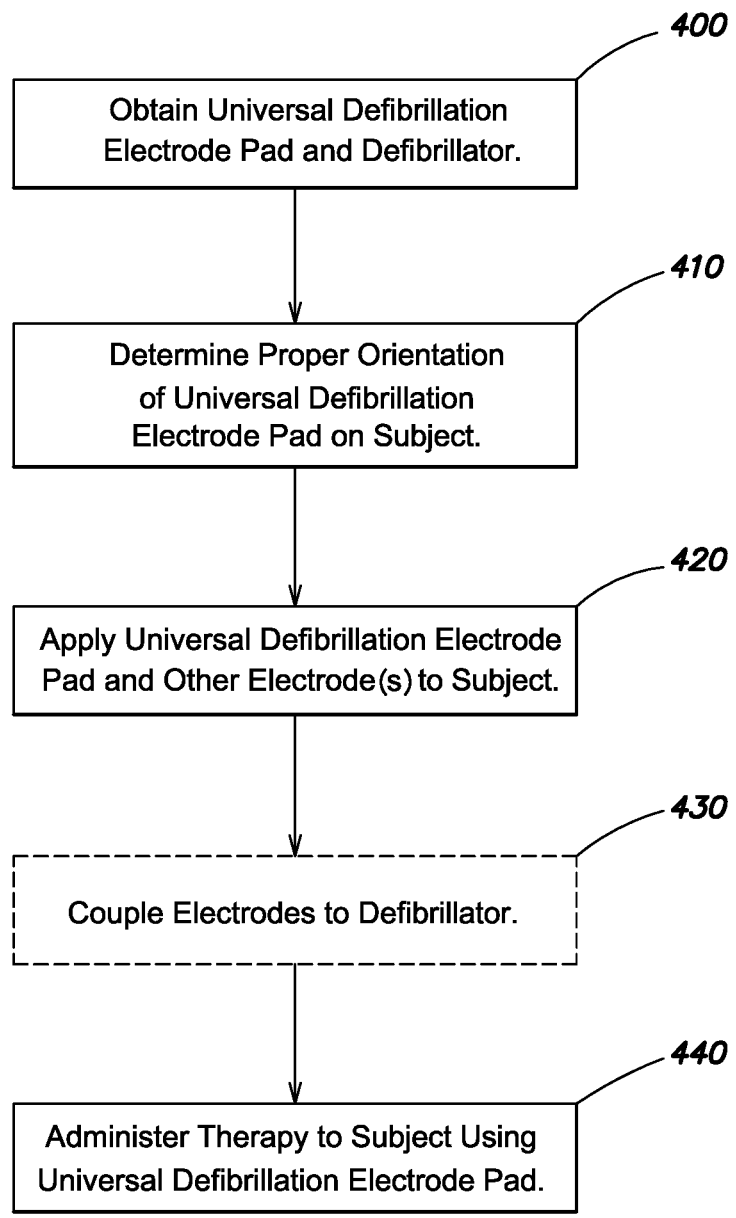
FIG. 4 is a flowchart of a method disclosed herein.

In accordance with another aspect, there is provided a method of providing treatment to a subject experiencing cardiac distress. A flowchart of the method is provided in FIG. 4. In a first act of the method (act 400), upon identifying a subject experiencing cardiac distress, a first responder may summon emergency assistance and proceed to obtain a defibrillator, for example an AED, and a universal defibrillation electrode pad. In some instances, the universal defibrillation electrode pad may be included with the defibrillator, and in other instances the defibrillator and universal defibrillation electrode pad may be obtained separately and/or from different locations.

In act 410, the first responder determines the proper orientation of the universal defibrillation electrode pad for the subject. The determination of the proper orientation of the universal defibrillation electrode pad may be informed by instructions included with the universal defibrillation electrode pad and/or by one or more markings on the universal defibrillation electrode pad. The universal defibrillation electrode pad may be oriented in a first orientation for an adult subject and in a second orientation for a pediatric subject.

In act 420 the first responder applies the universal defibrillation electrode pad to the subject in the determined orientation and also applies any other additional electrode pads to the subject as needed. In act 430, the first responder electrically couples the universal defibrillation electrode pad and any other electrodes to the defibrillator using, for example, cables and quick connectors which may extend from the universal defibrillation electrode pad and other electrode(s). In some embodiments, act 430 may precede act 420 or act 410, or may be eliminated, for example, when the universal defibrillation electrode pad and any other electrodes are supplied pre-coupled to a defibrillator. The first responder then performs CPR as needed on the subject and may also defibrillate the subject as needed (act 440). The performance of CPR, for example, the frequency and/or depth of chest compressions may be guided by feedback from a CPR assistance device applied to or included in the CPR administration section of the universal defibrillation electrode pad. The determination of the need for defibrillation and the timing of the defibrillation may in some instances be determined by the defibrillator.

Having thus described several aspects of at least one embodiment of this invention, it is to be appreciated various alterations, modifications, and improvements will readily occur to those skilled in the art. For example, it is to be appreciated that any of the features of any of the embodiments disclosed herein may be combined or substituted for features of any other embodiment disclosed herein. Acts of the method disclosed may be performed in alternate orders and one or more acts may be added to or omitted from the method or substituted by one or more alternative acts. Such alterations, modifications, and improvements are intended to be part of this disclosure, and are intended to be within the scope of the invention. Accordingly, the foregoing description and drawings are by way of example only.

What is claimed is:

1. A defibrillation electrode pad assembly comprising:
   a first defibrillation electrode pad comprising:
      an electrode section including at least one defibrillation electrode for delivering a defibrillation shock to a subject from a defibrillator electrically coupled to the at least one defibrillation electrode; and
      a CPR administration section mechanically coupled to the electrode section and including a region on which a responder may apply chest compressions to the subject, wherein the CPR administration section is configured to be mechanically decoupled from the electrode section; and
   a second defibrillation electrode pad delivering the defibrillation shock to the subject from the defibrillator,
   wherein the first defibrillation electrode pad is configured for placement on an adult subject, such that when both the electrode section and the CPR administration section are placed in a first position relative to each other on the adult subject, then the CPR administration section is configured to be at a location appropriate for the administration of chest compressions to the adult subject and the electrode section is configured to be at a location appropriate for the administration of the defibrillation shock to the adult subject;
   wherein the first defibrillation electrode pad is configured for placement on a pediatric subject, such that when both the electrode section and the CPR administration section are placed in a second position relative to each other on the pediatric subject, then the CPR administration section is configured to be at location appropriate for the administration of chest compressions to the pediatric subject and the electrode section is configured to be at a location appropriate for the administration of the defibrillation shock to the pediatric subject,
   wherein the second position is different from the first position, and
   wherein the first position of the electrode section and the CPR administration section relative to each other comprises a first orientation of the electrode section and the CPR administration section, and
   the second position of the electrode section and the CPR administration section relative to each other comprises a second orientation of the electrode section and the CPR administration section that is different from the first orientation.

2. The defibrillation electrode pad assembly of claim 1, wherein the location appropriate for the administration of the defibrillation shock to the adult subject is an apex position on the chest of the adult subject.

3. The defibrillation electrode pad assembly of claim 1, wherein the location appropriate for the administration of chest compressions to the adult subject is located above the sternum of the adult subject.

4. The defibrillation electrode pad assembly of claim 1, wherein the location appropriate for the administration of chest compressions to the pediatric subject is located above the sternum of the pediatric subject.

5. The defibrillation electrode pad assembly of claim 1, wherein the CPR administration section is mechanically coupled to the electrode section by a bridge of material.

6. The defibrillation electrode pad assembly of claim 5, wherein the bridge of material comprises a weakened portion.

7. The defibrillation electrode pad assembly of claim 6, wherein the weakened portion comprises one of: one or more perforations; a thinned portion of the bridge of material; or score lines formed in the bridge of material.

8. The defibrillation electrode pad assembly of claim 1, wherein the CPR administration section includes a displacement sensor.

9. The defibrillation electrode pad assembly of claim 8, wherein the displacement sensor comprises an accelerometer.

10. The defibrillation electrode pad assembly of claim 8, wherein the CPR administration section includes a CPR assistance device configured to provide feedback regarding frequency and/or depth of chest compressions applied to the subject on which the defibrillation electrode pad assembly is disposed during administration of CPR to the subject.

11. The defibrillation electrode pad assembly of claim 1, further comprising indicia of a proper positioning of the defibrillation electrode pad assembly for the adult subject and a proper positioning of the defibrillation electrode pad assembly for the pediatric subject.

12. The defibrillation electrode pad assembly of claim 11, wherein the indicia is provided on a label that is provided on a portion of the defibrillation electrode pad assembly.

13. The defibrillation electrode pad assembly of claim 11, wherein the indicia is provided as markings on a portion of the defibrillation electrode pad assembly.

14. The defibrillation electrode pad assembly of claim 11, wherein the markings are printed on a portion of the electrode section.

15. The defibrillation electrode pad assembly of claim 11, wherein the indicia comprises graphical representations of the proper positioning of the defibrillation electrode pad assembly for the adult subject and the proper positioning of the defibrillation electrode pad assembly for the pediatric subject.

16. The defibrillation electrode pad assembly of claim 1, further comprising indicia of a proper orientation of the defibrillation electrode pad assembly for the adult subject and a proper orientation of the defibrillation electrode pad assembly for the pediatric subject.

17. The defibrillation electrode pad assembly of claim 16, wherein the indicia comprises graphical representations of the proper orientation of the defibrillation electrode pad assembly for the adult subject and the proper orientation of the defibrillation electrode pad assembly for the pediatric subject.

18. The defibrillation electrode pad assembly of claim 1, wherein the first orientation is rotated by approximately 180 degrees from the second orientation.

19. The defibrillation electrode pad assembly of claim 1, further comprising the defibrillator for delivering the defibrillation shock to the subject via the at least one defibrillation electrode.

20. A defibrillation electrode system comprising:
a defibrillator for delivering a defibrillation shock to a subject;
a first defibrillation electrode pad comprising:
an electrode section including at least one defibrillation electrode for delivering the defibrillation shock to the subject from the defibrillator electrically coupled to the at least one defibrillation electrode; and
a CPR administration section mechanically coupled to the electrode section and including a region on which a responder may apply chest compressions to the subject, wherein the CPR administration section is configured to be mechanically decoupled from the electrode section; and
a second defibrillation electrode pad delivering the defibrillation shock to the subject from the defibrillator,
wherein the first defibrillation electrode pad is configured for placement on an adult subject, such that when both the electrode section and the CPR administration section are placed in a first position relative to each other on the adult subject, then the CPR administration section is configured to be at a location appropriate for the administration of chest compressions to the adult subject and the electrode section is configured to be at a location appropriate for the administration of the defibrillation shock to the adult subject;
wherein the first defibrillation electrode pad is configured for placement on a pediatric subject, such that when both the electrode section and the CPR administration section are placed in a second position relative to each other, on the pediatric subject, then the CPR administration section is configured to be at a location appropriate for the administration of chest compressions to the pediatric subject and the electrode section is configured to be at a location appropriate for the administration of the defibrillation shock to the pediatric subject,
wherein the second position is different from the first position, and
wherein the first position of the electrode section and the CPR administration section relative to each other comprises a first orientation of the electrode section and the CPR administration section, and
the second position of the electrode section and the CPR administration section relative to each other comprises a second orientation of the electrode section and the CPR administration section that is different from the first orientation.

21. The defibrillation electrode system of claim 20, wherein the location appropriate for the administration of chest compressions to the adult subject is located above the sternum of the adult subject, and the location appropriate for the administration of chest compressions to the pediatric subject is located above the sternum of the pediatric subject.

22. The defibrillation electrode system of claim 20, wherein the CPR administration section is mechanically coupled to the electrode section by a bridge of material.

23. The defibrillation electrode system of claim 22, wherein the bridge of material comprises a weakened portion.

24. The defibrillation electrode system of claim 23, wherein the weakened portion comprises one of: one or more perforations; a thinned portion of the bridge of material; or score lines formed in the bridge of material.

25. The defibrillation electrode system of claim 20, wherein the CPR administration section includes a displacement sensor.

26. The defibrillation electrode system of claim 25, wherein the displacement sensor comprises an accelerometer.

27. The defibrillation electrode system of claim 25, wherein the CPR administration section includes a CPR assistance device configured to provide feedback regarding frequency and/or depth of chest compressions applied to the subject on which the first defibrillation electrode pad is disposed during administration of CPR to the subject.

28. The defibrillation electrode system of claim 20, further comprising indicia of a proper positioning of the first defibrillation electrode pad for the adult subject and a proper positioning of the first defibrillation electrode pad for the pediatric subject.

29. The defibrillation electrode system of claim 28, wherein the indicia is provided on a label that is provided on a portion of the first defibrillation electrode pad.

30. The defibrillation electrode system of claim 28, wherein the indicia is provided as markings on a portion of the first defibrillation electrode pad.

31. The defibrillation electrode system of claim 28, wherein the indicia comprises graphical representations of a proper orientation of the first defibrillation electrode pad for the adult subject and a proper orientation of the first defibrillation electrode pad for the pediatric subject.

* * * * *

UNITED STATES PATENT AND TRADEMARK OFFICE
CERTIFICATE OF CORRECTION

| | |
|---|---|
| PATENT NO. | : 11,291,830 B2 |
| APPLICATION NO. | : 16/231443 |
| DATED | : April 5, 2022 |
| INVENTOR(S) | : Gary A. Freeman et al. |

It is certified that error appears in the above-identified patent and that said Letters Patent is hereby corrected as shown below:

On the Title Page

Item (63) Column 1, Line 11, delete "10,201,696" and insert -- 10,201,696, --

In the Claims

Column 9, Line 51, Claim 14, delete "claim 11," and insert -- claim 13, --

Signed and Sealed this
Twenty-sixth Day of July, 2022

*Katherine Kelly Vidal*

Katherine Kelly Vidal
*Director of the United States Patent and Trademark Office*